US007976685B2

(12) United States Patent  (10) Patent No.: US 7,976,685 B2
Wartelle  (45) Date of Patent: Jul. 12, 2011

(54) REMOTE CONTROLLABLE POT TENDING MODULE FOR USE IN ALUMINUM PRODUCTION PLANTS

(75) Inventor: Benoit Wartelle, La Madeleine (FR)

(73) Assignee: E.C.L., Ronchin (FR)

( * ) Notice: Subject to any disclaimer, the term of this patent is extended or adjusted under 35 U.S.C. 154(b) by 1175 days.

(21) Appl. No.: 11/678,198

(22) Filed: Feb. 23, 2007

(65) Prior Publication Data

US 2007/0205104 A1   Sep. 6, 2007

Related U.S. Application Data

(60) Provisional application No. 60/778,382, filed on Mar. 3, 2006.

(51) Int. Cl.
*C25C 7/00*   (2006.01)

(52) U.S. Cl. .................. 204/247; 204/245; 204/279

(58) Field of Classification Search .................. 204/245, 204/279; 205/389, 392
See application file for complete search history.

(56) References Cited

U.S. PATENT DOCUMENTS

| 5,435,897 | A | 7/1995 | Zannini |
| 6,864,903 | B2 | 3/2005 | Suzuki |
| 2004/0211663 | A1 | 10/2004 | Gagne et al. |
| 2005/0281644 | A1 | 12/2005 | Lussen et al. |

FOREIGN PATENT DOCUMENTS

| WO | 2005/052217 A1 | 6/2005 |
| WO | 2005052217 | 6/2005 |

OTHER PUBLICATIONS

Dhong et al, "Structure from Stereo-a Review", IEEE Transactions on Systems, Man and Cybernetics, IEEE Inc., vol. 19, No. 6, Nov. 1989, pp. 1489-1510.

*Primary Examiner* — Harry D Wilkins, III
*Assistant Examiner* — Zulmariam Mendez
(74) *Attorney, Agent, or Firm* — Dennison, Schultz & MacDonald (57) ABSTRACT

Pot tending module (7) for a series of electrolytic cells for production by igneous electrolysis, including a chassis (8) that can be fixed to a trolley (6) moving along a travelling crane (4) and provided with a set of tools, particularly including at least one anode handling device (11), which is also provided with at least two display means (41 and 42) capable of taking views and transmitting them in the form of electromagnetic signals, typically two video cameras, the display means disposed at a distance from each other and from the working area, to be able to aim at the working area (23) of the anode handling device(s) along two non-parallel directions (D1) and (D2), forming an angle preferably close to 90°. This pot tending module may also include a third camera (43) that presents an overview of the tools and working areas for these tools, and a fourth camera (44) fixed onto the base of the anode grab actuators.

21 Claims, 3 Drawing Sheets

REMOTE CONTROLLABLE POT TENDING MODULE FOR USE IN ALUMINUM PRODUCTION PLANTS

This application claims the benefit of U.S. Provisional Application Ser. No. 60/778,382 filed Mar. 3, 2006.

FIELD OF THE INVENTION

The invention relates to the production of aluminum by igneous electrolysis using the Hall-Héroult process. It particularly concerns remote control of "pot tending machines" (PTM) used in aluminum production plants.

DESCRIPTION OF RELATED ART

Aluminum is produced industrially by igneous electrolysis, in other words by electrolysis of the alumina in solution in a molten cryolite bath called an electrolyte bath, using the Hall-Héroult process. The electrolytic bath is contained in electrolytic cells that include a steel pot shell coated on the inside with refractory and/or insulating materials and a cathode assembly located at the bottom of the cell. Anodes, typically made of a carbonaceous material, are fixed to a superstructure provided with means of moving them vertically, said anodes being progressively consumed during the electrolysis process. The assembly composed of an electrolytic cell, its anodes and the electrolyte bath is called the electrolytic cell.

Plants contain a large number of electrolytic cells arranged in line in buildings called potrooms or halls, and electrically connected in series by means of connecting conductors so as to optimise the occupancy of plant floors. The cells are usually arranged in lines so that vehicles can move along a circulation aisle along the potroom. They comprise a series of anodes provided with a metallic stem that will be used to fix the anodes and electrically connect them to a metallic anode beam fixed to the superstructure.

During operation of an aluminum reduction plant, work has to be done on electrolytic cells including replacement of spent anodes by new anodes, drawing off of liquid metal from cells and drawing off or the addition of electrolyte. In order to do this work, the most modern plants are provided with one or several service units comprising a travelling crane that can be translated above the electrolytic cells, and a trolley that moves along the travelling crane and to which a tending module is fixed comprising handling and working devices (also called "tools") such as bucket wheels and pulley blocks. The tending module is placed above the area of the cell on which the work is to be done and the tools are brought in, typically using telescopic arms, to the working area itself along a trajectory that includes a substantially vertical downwards component. In the following, we will use X to denote the direction of the large side of a cell, Y the direction of the small side of the cell and Z the vertical direction. Said tending units are referred to as "Pot Tending Assemblies" "PTA" or "Pot Tending Machines" ("PTM").

At the present time, anode replacement operations require the presence of two operators:
  one operator who controls the travelling crane and PTM tools from an onboard cab; said onboard cab is usually fixed to the PTM: it moves with the PTM and it can be put into place such that it is facing and vertically above the anode to be replaced, the operator then having direct visual access to the working area;
  and an operator on the shop floor who performs all delicate tasks and tasks that cannot be done from the cab, for example due to insufficient visibility or technical difficulties making remote control of a particular tool impossible for a given specific operation. This operator is exposed to a number of risks related to the proximity of the electrolytic cell and the presence of handling tools, particularly PTM tools located close to the working area.

Typically, the operator in the onboard cab uses the following during anode replacements:
a) a chipping hammer attached to the PTM used to break the alumina and solidified bath crust that usually covers the anodes in the cell,
b) a bucket wheel attached to the PTM that clears away the anode location after removal of the spent anode, by removing solid materials (such as crust and carbon pieces and alumina) located in it;
c) one or more anode grabs attached to the PTM, used to grip and manipulate the anodes by their stems, particularly to remove spent anodes and to put new anodes into place in the electrolytic cell;

In general, the operator on the floor who sees the working area from a different angle, helps the operator to perform these manipulations. Furthermore, the operator on the floor grips a retractable duct also attached to the PTM used to add alumina and/or crushed bath into the electrolytic cell, so as to reform a cover layer after placement of a new anode.

Research has been undertaken so that these operations can be carried out by a single operator able to act in complete safety at a sufficient distance from the working area, with the objective of reducing operating costs and improving safety.

European application EP 0 618 313 (TECHMO) discloses a modular assembly for automatically replacing anodes. This assembly comprises a travelling crane, two modules on trolleys that move along the travelling crane, each module being dedicated to specific tasks, a tending vehicle and a transport vehicle each passing along an aisle located on each side of a row of cells. In this modular equipment, the tending vehicle comprises a control cab from which handling and working operations can be controlled. Note that this control cab can be fitted with a remote control system and a camera display system, although this aspect will not be described in more detail.

The first tests carried out by the applicant showed that the remote control of operations such as anode changes cannot be performed with any means for displaying the working area and transmitting orders to tools, because said means must necessarily enable the operator to act with the necessary reactivity. For example, means conventionally used in other technical domains, such as remote manipulation of radioactive loads, satisfy different constraints that do not correspond to the particular needs related to operations occurring during anode changes, particularly due to the need to take very fast action during said operations.

Furthermore, the modular assembly described in EP 0 618 313 requires a highly specific configuration of the potroom, for example with two circulation aisles on each side of the row of electrolytic cells.

The objective in application US2004/211663 (ALCOA) is different: the objective is to measure anode heights. In order to do this, in one particular embodiment it is suggested that vertical distances should be measured by means of three digital cameras installed on a mobile rigid arm.

The purpose of this invention is not to measure precise vertical distances, but to design a device for remote change of anodes that can be easily adapted to most existing potrooms and that can operate reliably with short response times, within the specific industrial context of an aluminum production plant by igneous electrolysis.

SUMMARY OF THE INVENTION

A first purpose of the invention is a pot tending module for a series of electrolytic cells designed for aluminum production by igneous electrolysis comprising a chassis that can be fixed onto a mobile assembly, typically a trolley moving along the travelling crane, and provided with a set of tools particularly including at least one anode handling device, the pot tending module being also provided with at least two display means capable of taking views and transmitting them in the form of electromagnetic signals, typically two video cameras, said display means being placed on said pot tending module such that they can view the working area of said anode handling device(s) along two different non-parallel directions D1 and D2, typically with an angle between them greater than 45°, and preferably close to 90°. More precisely, according to the invention, a first display means is placed such that it can aim at the working area along the direction (D1) of a straight line contained in one vertical plane (V1) and a second display means is placed such that it can aim at the working area along the direction (D2) of a straight line contained in a vertical plane (V2), the planes (V1) and (V2) not being parallel, their intersection being a vertical straight-line passing through the working area. The angle between the vertical planes (V1) and (V2) is as large as possible, typically more than 45°, and preferably between 60° and 90°.

The pot tending module according to the invention is provided with display means that enable remote control of the tools with which it is equipped, without the need for an operator located inside an onboard cab fixed to said pot tending module. If the operator remains in said onboard cab of the pot tending module, he cannot physically carry out urgent operations that have to be done by the operator on the ground. Therefore as described in EP 0 618 313, the operations need to be controlled from the ground so that action can be taken on the cell if necessary without being obliged to use a vehicle on the ground with an onboard control cab. But the operator on the ground must be able to have visual access to the working area, at least as good as the visual access available to the operator in the cab onboard the PTM.

For all operations that take place during the change of anodes and that at the moment are controlled from the cab onboard the PTM (chipping of the alumina and the molten bath crust around the anode; removal of solid pieces in the location left by the removed anode that might contain crust and carbon debris, and alumina; gripping and manipulation of anodes by their stem), it is important to have a good estimate of the distances in space, in other words both horizontal distances and vertical distances. According to the invention, at least two display means are used to display the working area from two different locations, each along a direction in a vertical plane passing through the working area. Thus, the operator can evaluate distances, avoid collisions between tools and reach the objective with good precision.

The most difficult of all of these operations is undoubtedly gripping the anode stem, and the number and position and the viewing direction of said display means according to the invention are selected primarily to facilitate this operation.

The handling device designed for handling and displacement of anodes is used particularly for picking up spent anodes and placement of new anodes in the electrolytic cell. It usually comprises a grab capable of gripping the anode. This grab is placed close to the end of the anode stem that will be picked up, and is then closed on said end, the anode thus gripped then possibly being lifted and transported outside the electrolytic cell, typically to be taken to the anode recycling shop. The anode handling grab is typically provided with two gripping devices that pivot about a common axis or about axes substantially parallel. The direction (P) of the common axis or the parallel axes is substantially horizontal. These two devices form a jaw that has an open configuration, wherein the ends of said devices delimit an opening typically facing downwards and in which the upper end of the stem may be inserted, and a closed configuration in which the ends of said devices bear laterally on the stem such that said stem is trapped and held in place.

The ends of the jaw gripping devices define a contour that globally follows the shape of the section of the end of the anode stem. This section is usually rectangular, one of the sides of the rectangle corresponding to the contact surface of the anode stem on the anode beam. When the grab closes on the end of the stem, the direction (P) of the pivot axis of the grab gripping elements is, or becomes, oriented along the direction of one (L) or the other (l) of the sides of the rectangular section of the stem.

In general, the anode grab is designed with a fixed axis (P) relative to the beam. In this case, one of the directions D1 or D2 is preferably substantially parallel to said axis. But if the anode grab is designed to maintain a degree of freedom of rotation about a vertical axis, the axis (P) is not fixed with respect to the beam and under these conditions it is preferable to define the directions D1 and D2 relative to the electrolytic cell rather than directly with respect to the beam, which can easily be done because the pot tending module must be in a precise fixed position with respect to the mobile assembly to which it is attached (typically the trolley) and that is oriented such that said pot tending module is located nearby and vertically above the anode to be changed before the tools are activated. Thus for example, the directions D1 and D2 may substantially correspond to the directions X and Y of the large and small sides of the electrolytic cell once the tending module is positioned to work on a given anode.

Preferably, the viewing directions D1 and D2 of the two display means substantially correspond to the directions (L) and (l) of the sides of the rectangular section of the anode stem, when the PTM is in position to work on a given anode.

When the pot tending module is provided with a single anode gripping device, each of the two display means is preferably placed in a vertical plane that, when the PTM is positioned to work on a given anode, passes through a median plane of the rectangular section of the anode stem. Said display means that we will subsequently called cameras, are placed at the lowest possible height above the cell, preferably on or slightly above the so-called "safety level" that defines an elevation above which any lower end of the tool must be when the PTM has to move above the electrolytic cells.

When the pot tending module is provided with several anode gripping devices, and these devices are in position to work on the anodes to be replaced, they are aligned along the anode stem alignment direction that itself coincides with the direction of the anode beam, in other words the direction X of the large side of the electrolytic cell with which one of the sides (L or l) of the rectangular section of the anode stem is substantially parallel. In this case, one of the cameras is placed in the vertical plane that contains the alignment direction of the gripping devices and that, when the PTM is in position to work on the anodes to be replaced, coincides with the common median plane of the aligned anode stems, that is itself parallel to the anode beam. The other camera is placed in a vertical plane substantially perpendicular to the previous plane and passing through the centre of gravity of the gripping devices. The cameras are as low as possible above the cell, preferably at or slightly above the safety level, typically by about a hundred millimeters. Although located at a low height, they are several meters vertically above the working area, so that for example the first camera (located in the common median plane of the anode stems) is able to display both the closest grab and the following anode grabs. There are two possible ways of improving the visibility of the following grab(s):
a) the first camera is very slightly offset from the grab alignment plane;
b) each anode hooking or unhooking is made by successive steps, beginning with the anode furthest from the camera and progressively moving towards the first camera.

In general, gripping devices are moved vertically either by gravity or by using vertical telescopic arms. The first camera is then aligned with the vertical axes on which said gripping devices are actuated and the second camera is placed perpendicular to this alignment direction, in the vertical plane that typically passes in the middle of said gripping devices.

The two cameras fixed to the tending module but located in two different locations at a distance from each other and from the working area (in other words all points corresponding to possible low positions of said anode gripping unit(s)) must be able to aim at the working area from two directions, preferably substantially orthogonal to each other. The first camera can take a view fixed in elevation, azimuth and zoom, defined once and for all as a function of all said possible low positions of said anode gripping unit(s). The second camera "facing" the anode grab(s) is preferably motor driven in elevation (rotation possible about a horizontal axis), in azimuth (rotation possible about a vertical axis), and in zoom such that different view taking conditions can be defined as a function of the operation to be done, because the tending module is preferably also provided with other tools and said second camera must also be able to display their working area. In general, the first camera and the second camera must be able to be placed fairly far from the active part of the tools so as to give good visibility in the action field of the tools.

The tending module may be provided with other tools, particularly:
a) a chipping hammer used to break the alumina and solidified bath crust that usually covers anodes in the cell;
b) a bucket wheel that clears the anode location after removal of the spent anode, by removal of solid materials (such as crust and carbon pieces and alumina) located in this area;
c) a hopper associated with a retractable duct used to add alumina and/or crushed bath into the electrolytic cell, so as to reform the cover layer after placement of a new anode;
d) a heavy lifting tool such as a pulley block.

At least for the second camera, the precise viewing conditions (viewed area, scale) may be defined specifically during the manipulation by the operator or preferably may be predefined as a function of the tool chosen by the operator.

The movement angle in elevation is typically between −60° and +60° from the vertical plane passing through D2, so that the second camera can easily observe all tools used with the tending module. Similarly, the movement angle of the second camera in elevation is between 0° and −80° from the horizontal plane, so that the tool can be monitored as it moves downwards towards the working area or on the contrary, can be monitored as it is lifted, particularly when the grab is lifted with the spent anode. The zoom magnification factor of the second camera is advantageously between 1 and 25.

Preferably, the first camera is placed on the PTM in the vertical plane P1 that, when the PTM is in position to operate on a given anode, coincides with the plane of symmetry of alignment of the anode stems, parallel to the anode beam. It is placed at an elevation substantially equal to the safety level, typically equal to 3 meters and located outside the outermost of the gripping devices, typically at a horizontal distance of between 1 and 3 meters from it, and preferably equal to approximately 1 meter.

Preferably, the second camera is placed on the PTM in the vertical plane P2 that, when the PTM is in position to operate on a given anode, is perpendicular to plane P1 and passes through the centre of gravity of the gripping devices, at an elevation substantially equal to the safety level, typically equal to 3 meters, and in a position which is on the opposite side of the centre of gravity of said gripping devices from the face of the corresponding grab(s) that, when the PTM is in position to work on the given anode(s), is facing the anode stems(s) that will come into contact with the anode beam, typically at a horizontal distance from said centre of gravity equal to between 2 and 4 meters, and preferably substantially equal to 3 meters.

In the preferred embodiments of the invention, the pot tending module comprises a chassis, typically a platform that can be fixed to a mobile assembly and at least one turret fitted on the chassis so that during use it can be pivoted about a vertical axis A. Said turret is provided with a specific set of tools like those mentioned above. It may also be provided with two cameras that in this case are therefore located in a fixed position with respect to the tools. But said cameras may also be placed on a second turret independent of the first, coaxial with it and outside it, in other words surrounding the first turret and capable of rotating about the same vertical axis A.

A single turret can give a compact module in which the tools are placed close to the turret rotation axis, without excessively reducing visibility. It can also make operations symmetrical, so that such a compact module can be used indifferently regardless of the position of the cells with respect to the sides of the potroom and regardless of the position of the anode to be replaced in the cell.

A module with two turrets is more difficult to design, and is more expensive and less compact but it can give a better visibility and move at least one camera relative to the tools so as to obtain a better viewing angle.

Optionally, the pot tending module according to the invention comprises a third camera placed not far from the second camera that will present an overview of tools in the module and working areas for these tools.

Optionally, the pot tending module according to the invention comprises another camera placed close to the actuator of one of the anode gripping devices, typically fixed onto the base of the telescopic arm that actuates said gripping device, and aimed at a zone that includes the low position of said gripping devices(s).

Images seen by the cameras are transmitted in the form of analog data, or preferably digital data, to a system or a set of signal processing systems and this results in the creation of images displayed on screens placed outside the pot tending module. Advantageously, the pot tending module is provided with a central image processing device connected to cameras, typically through shielded cables, and that processes received images such that it can associate them by grouping them in the form of a single digital image ("page layout"), that is then advantageously compressed in standard video image compression formats (MPEG, JPEG, etc.). Advantageously, said central image processing device is associated with a transmitter that transmits digital files associated with the video images (advantageously compressed) in the form of electromagnetic waves, preferably airborne, to receivers located outside the pot tending module and provided with screens.

In order to improve the safety of the remote control of the pot tending module, said central processing device of images perceived by the cameras processes the signal such that a number identifying the pot tending module with which it is associated is inset into at least one area, preferably a peripheral area, of the transmitted image and/or the transmitter— that transmits digital files associated with the video images— transmits in a frequency or a plurality of specific frequencies representative of the pot tending module with which the transmitter is associated.

Another purpose of the invention is a pot tending machine comprising a mobile element, typically a trolley, and a tending module like that described above.

Another purpose of the invention is a pot tending unit for an aluminum production plant by igneous electrolysis that comprises a travelling crane and at least one tending machine comprising a trolley that can move along said travelling crane and a pot tending module according to the invention.

Another purpose of the invention is the use of a tending unit according to the invention for performing work on electrolytic cells designed for the production of aluminum by igneous electrolysis, particularly for anode replacement operations.

Another purpose of the invention is a system for assistance with control over handling and work operations on an electrolytic cell, typically intended for the replacement of anodes, said system comprising:
  a tending unit itself comprising a pot tending module and moved using motor driven actuators, said tending module being provided with tools actuated by motors, said tending unit being provided with display means,
  a control module provided with at least one monitor reproducing the image of the working area taken by at least one camera and
  a control module capable of transmitting orders to actuators in the pot tending unit, wherein:
  a) said pot tending module is a pot tending module according to the invention provided with a device processing images perceived by cameras, associated with a transmitter transmitting signals associated with the digital images in the form of electromagnetic waves, preferably radio waves;
  b) said control module is provided with a receiver capable of receiving said electromagnetic waves and at least one monitor that presents at least the image from one of the two cameras with a minimum definition of 350,000 pixels preferably, using the standard 2:3 format, with a minimum definition of 768*512 pixels, and even better with a minimum definition of 1024*768 pixels.

The screen size is essentially dependent on the size of the control module and the working space available to the operator. Typically, the monitor is a digital screen with a diameter of more than 12", and preferably at least equal to 14".

Optionally, said monitor may also display the image of the other camera on request at any time, with an identical minimum definition. Also preferably, said monitor has a sufficient area to simultaneously present the two images with the same definition, the adjacent assembly typically occupying a minimum diagonal of 17", and preferably 20".

Obviously, said image processing device for processing of images perceived by the cameras may be a central device, typically connected to the cameras through shielded cables and that processes received images such that it can associate them by grouping them in the form of a single digital image ("page layout"), that is then advantageously compressed into a video image compression format (MPEG, JPEG, etc.).

Advantageously, the transmission system between the transmission device in the pot tending module that transmits video images and the reception device associated with the monitor(s) of the control module is a spread spectrum digital transmission system, typically the digital modulation system called COFDM (Coded Orthogonal Frequency Multiplex). The information is decomposed in coded digital form so that it can be distributed on several orthogonal carrier waves. Thus, very narrow frequency sub-channels are created and the signals thus transmitted that have a low probability of all being disturbed at the same time, are reprocessed digitally after reception so as to reconstruct the complete information. Such a system can have response times of less than 200 ms, so that the operator can react in time as a function of what he sees on the screen.

In order for remote control of tools taking placed during anode replacement operations to be done efficiently, the operator must firstly have perfect vision of the working area, but also there must be no long time lags between an event, the image that represents this event on the screen, and the signal that leads to a correction movement of the tool actuator: the operator must be able to see every incident, he must have a minimum time to react and his order to correct the current manipulation must be transmitted to the actuator in time. The applicant has observed that a purely digital transmission results in a response time of the order of 500 ms or even longer, which is not sufficient considering the operational constraints related to replacement of anodes. A purely analog transmission can give significantly shorter response times but the applicant has observed that the analog transmission in the particular environment of an electrolytic cell is subject to severe disturbances, so that a reliable remote control system cannot be obtained. This is why the applicant has developed the solution described above that combines the speed of analog transmission with the reliability of digital transmission.

In one embodiment of the invention, the control module is also provided with a monitor that enables viewing of the field filmed by the third camera, and/or a monitor enabling a view of the field filmed by the fourth camera associated with anode gripping devices and fixed close to the base of the actuator of one of the gripping devices. Preferably, the image of this third camera and the image of the fourth camera are also transmitted with sufficient definition corresponding to a minimum of 350,000 pixels. In one preferred embodiment of the invention, the control module is provided with a sufficiently large screen to simultaneously provide three or four images, the first two images each occupying an area defined by a diagonal greater than or equal to 12".

Said control module is in the form of an easily portable remote control box provided with buttons. It is used to control movement of the travelling crane, the trolley, the turret(s) of the pot tending module, the cameras and the tools, preferably mounted on telescopic arms. It is fitted with a transmitting device transmitting controls to the various actuators. Some controls are directly related to a particular action of a tool, others may be induced by this action. For example, if the operator chooses a particular action to be carried out by a given tool, the system can automatically put one or several cameras into operation, with a predefined setting of the display parameters.

In one embodiment of the invention, said instrumentation module and said control module are installed in a vehicle that moves along the circulation aisle of the potroom.

In another embodiment of the invention, the potroom is provided with a plurality of instrumentation modules located in fixed cabs, each associated with a group of n cells (where n is typically between 2 and 10); the operator carries the control module and moves to the cab associated with the cell concerned by the anode change. The operator installs said control module in said cab, connecting it such that the control assistance system in said cab is made fully operational and can thus function.

Removed control devices of the control module are matched with the machines: a channel and an address are assigned to each control—actuator pair. The signal transmission system between cameras and monitors of the instrumentation module is not necessarily the same as the system for transmission of controls between the control module and the different actuators of the travelling crane, the trolley, the turret(s), the cameras, telescopic arms and tools. The first system is required to manage transmission of a much greater data flow than the second, even if the remote control orders require security which for example may involve some redundancy of the transmitted information. Therefore, a "conventional" system can be used for transmission of remote controls, preferably a digital system to prevent disturbances related to the particular electrolysis environment.

However, in the case in which a COFDM type system is used for transmission of images, it appears advantageous to also use it to transmit the controls to the different actuators of the tending unit (travelling crane, trolley, pot tending module: turret, cameras, telescopic arms and tools).

Another purpose of the invention is a method of replacing the anode of an electrolytic cell intended for production of aluminum by igneous electrolysis, in which at least one specific anode is replaced by a new anode, using the control assistance system according to the invention as described above.

BRIEF DESCRIPTION OF THE DRAWINGS

The invention is described in detail below, with reference to the attached figures, in which.

EXAMPLE

Figure 1:
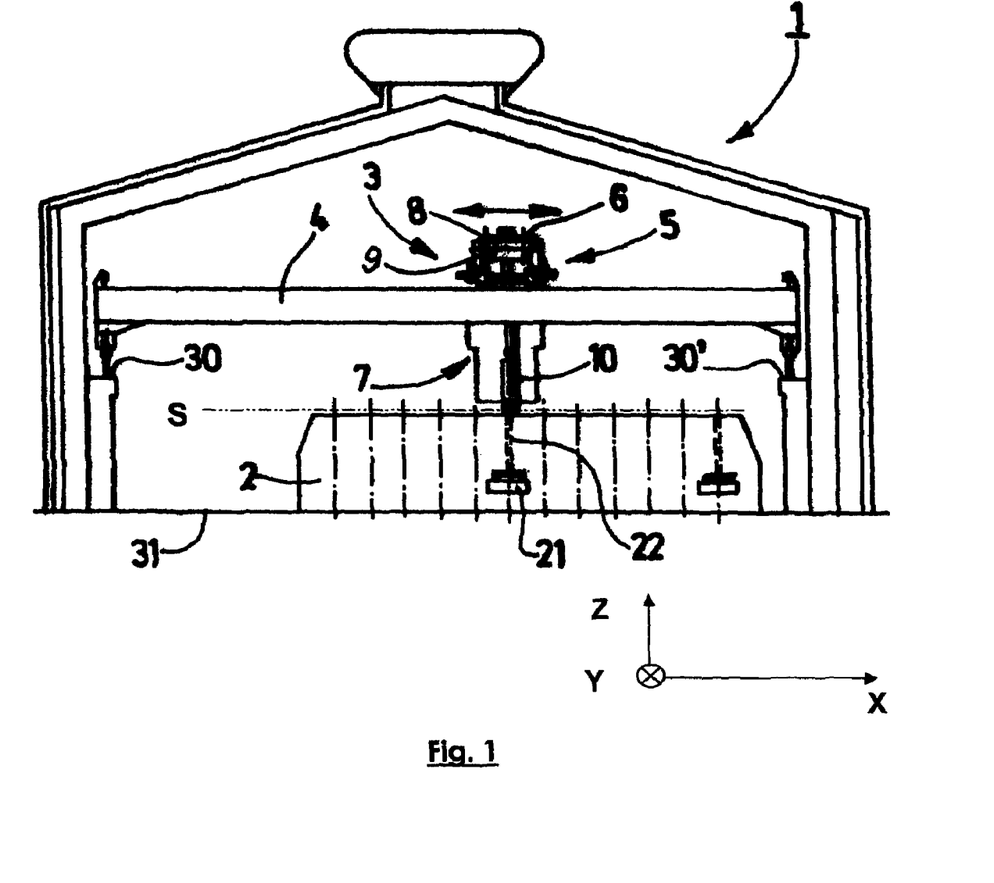
FIG. 1 illustrates a sectional view of a typical potroom, designed for production of aluminum and including a tending unit shown diagrammatically.
Figure 2:
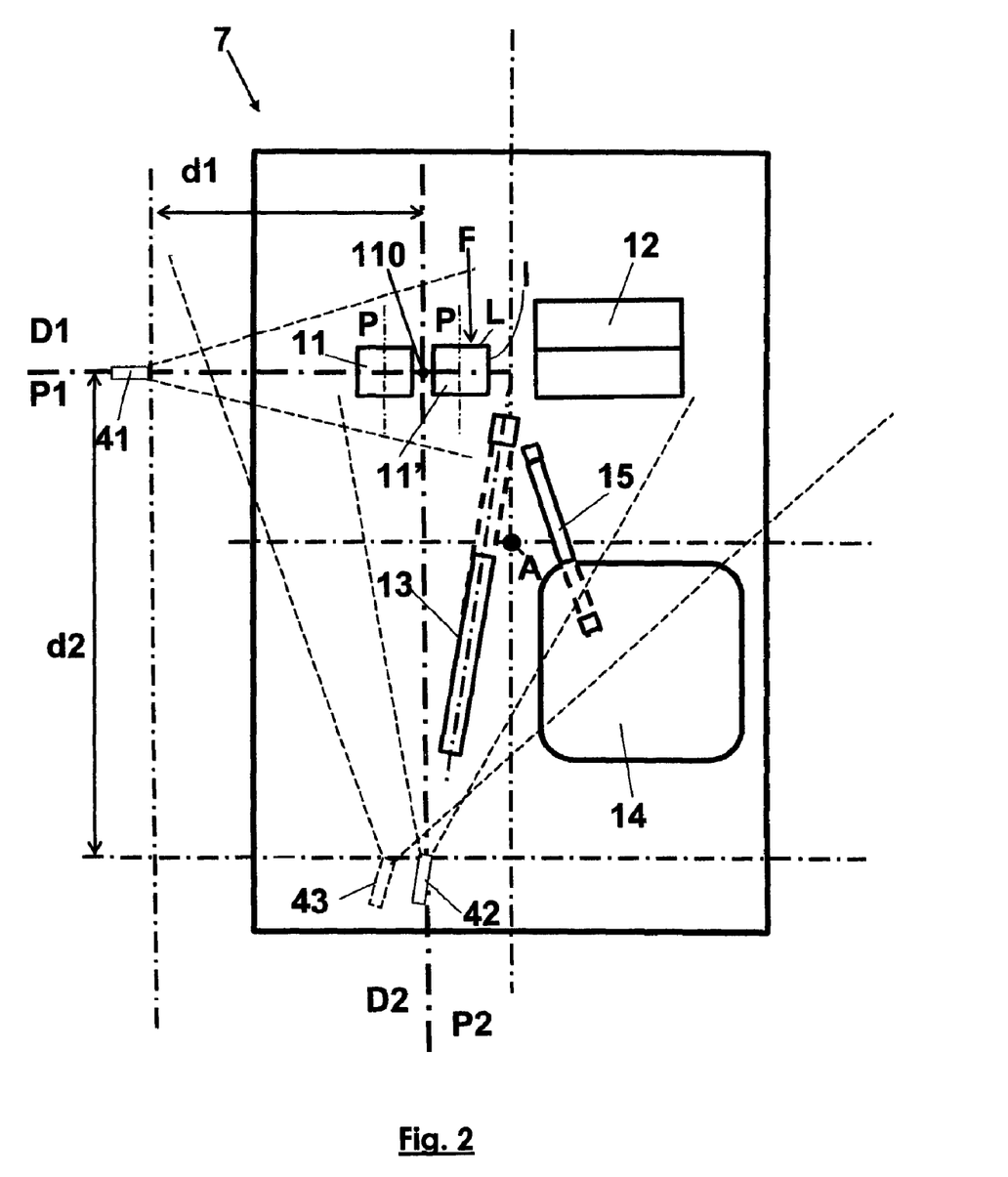
FIG. 2 is a bottom view diagrammatically showing one particular arrangement of the basic tools and three cameras in a pot tending module according to the invention.
Figure 3:
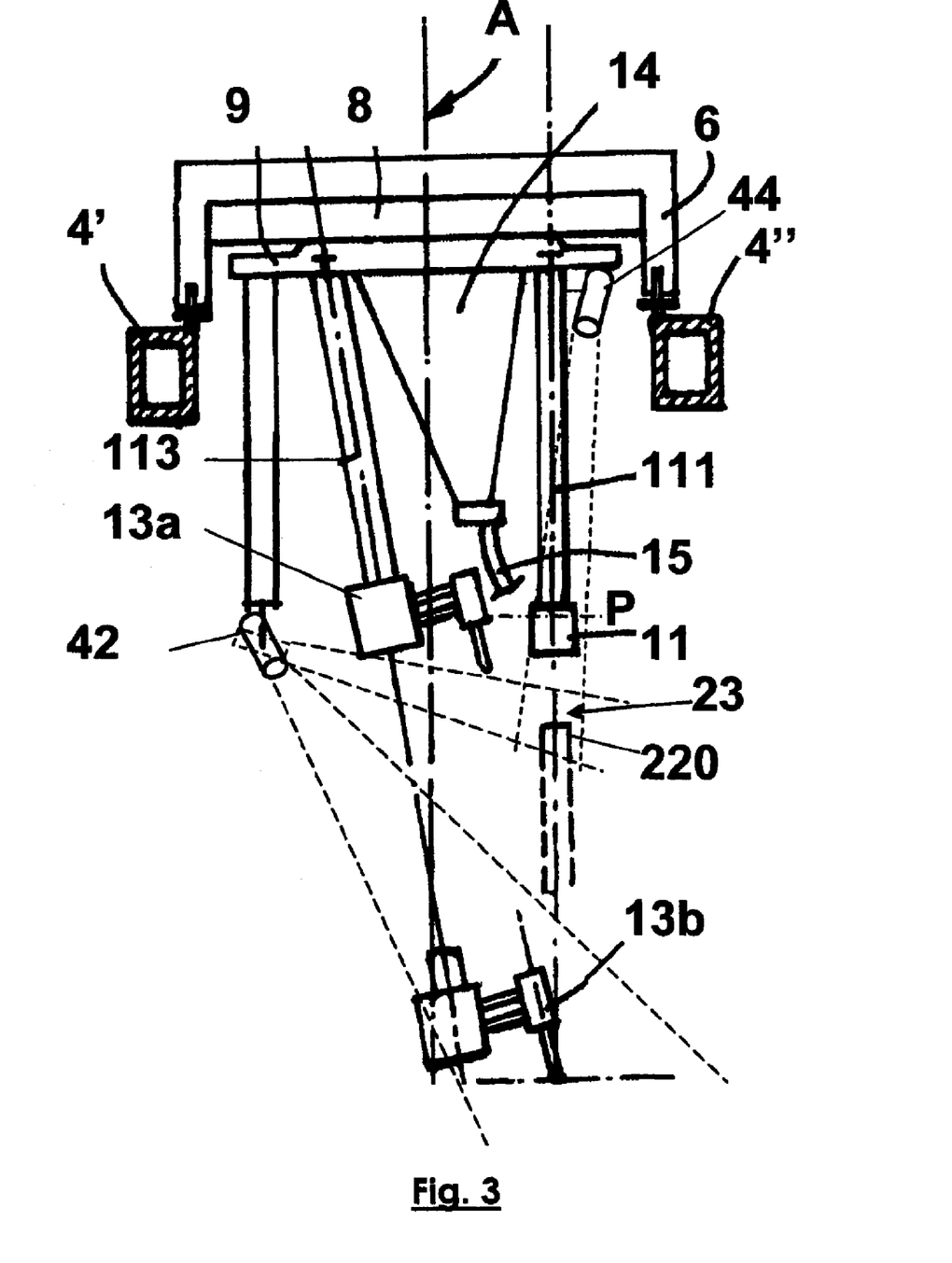
FIGS. 3 is a side view diagrammatically showing the pot tending module of FIG. 2.

FIGS. 1 to 3

Electrolysis plants intended for aluminum production comprise a liquid aluminum production zone that includes one or several potrooms (1). As shown in FIG. 1, the potroom (1) comprises electrolytic cells (2) and at least one "tending unit" or "tending machine" (3). The electrolytic cells (2) are normally arranged in rows or lines, each row or line typically comprising more than a hundred cells. The cells (2) are arranged so as to leave a circulation aisle (31) clear along the potroom (1). The cells (2) comprise a series of anodes (21) provided with a metal stem (22) designed for hooking or electrical connection of the anodes to a metallic anode beam (not shown).

The tending unit (3) is used to carry out operations on the cells (2) such as anode changes, or to fill in feed hoppers of electrolytic cells with crushed bath and AlF3. It may also be used to handle various loads, such as pot elements, liquid metal ladles or anodes. The invention is particularly applicable to tending units that will be used to perform anode changes.

The tending unit (3) comprises a travelling crane (4) that may be moved in translation above the electrolytic cells (2) and a tending machine (5) comprising a mobile trolley (6) that may be moved on the travelling crane (4) and a pot tending module (7) provided with several handling and work devices (10) such as tools (bucket wheels, anode gripping units, also called anode grabs, chipping hammers, etc.). The travelling crane (4) is supported on and travels on running tracks (30, 30') arranged parallel to each other and to the main axis of the hall (and the line of cells). In the geometric configuration in this example, the direction of the main axis of the hall corresponds to the (Y) direction of the small side of a cell. During displacement of the tending module above the electrolytic cells, the tools are arranged on said pot tending module such that their bottom end is always above a certain height corresponding to a safety level (S).

The pot tending module (7) comprises a chassis (8) fixed onto a trolley (6) that moves along the travelling crane (4) (along the X direction of the large side of the electrolytic cell). This chassis is provided with a set of tools (10) including two anode handling devices (11 and 11') and four cameras (41, 42, 43 and 44) that give a remote display of the working areas of said anode handling devices, along at least two directions (D1) and (D2) substantially perpendicular to each other.

The anode grab (11) is in the form of a jaw for which the ends of the pivoting elements define a contour that is globally equivalent to the square shape of the section of the end of the anode stem. The direction (D2) is chosen such that it is parallel to the direction (P) of the pivot axis of the grab gripping elements. Consequently, the second camera (42) sees a substantially front view of the grab.

In this case, the tending module is provided with two anode grabs (11 and 11') that, when they are in position to work on the anodes to be changed, are aligned along the alignment direction of the anode stems, that itself is coincident with the direction of the anode beam, in other words the X direction of the long side of the electrolytic cell, this cell being substantially parallel to the side L of the rectangular section of the anode stem. When the PTM is put into place to work on a given anode, the viewing directions (D1) and (D2) of the two cameras (41) and (42) are coincident with the directions (L) and (l) of the sides of the square section of the anode stem.

The first camera (41) is placed in the vertical plane that contains the alignment direction of the anode grabs, or rather near to this plane (typically at a distance of about a hundred millimeters) to facilitate the vision of the most remote anode grab (11'). This plane that coincides with the median plane common to the anode stems, parallel to the anode beam (not shown) when the PTM is put into place to work on the anodes to be changed, corresponds substantially to the plane (V1) that contains the first viewing direction (D1). The second camera (42) is placed in a vertical plane (P2) perpendicular to the previous plane and passing through the middle (110) of the anode grabs (11) and (11'). The second camera (42) aims at the working area along a direction (D2) included in a vertical plane (V2) that coincides with (P2) or makes a small angle with it (case shown in FIG. 2). The cameras (41), (42) and (43) are placed at a height corresponding to the safety level (S), typically three meters above the ground.

The anode grabs (11 and 11') are moved vertically by vertical telescopic arms (111). The first camera (41) is then located along the alignment of the vertical telescopic arms and the second camera (42) is placed perpendicular to this alignment direction, in a vertical plane that typically passes through the middle (110) of the grabs. The two cameras are adjusted so that at least the set of points corresponding to the possible low positions of the anode grabs can be seen.

The first camera (41) takes a fixed view in elevation, in azimuth and in zoom, defined once and for all. The second camera (42) located "facing" the anode grabs is motor driven in azimuth (rotation possible about a vertical axis), in elevation (rotation possible about a horizontal axis) and in zoom such that the different viewing conditions can be defined as a function of the operation to be done.

The first camera (41) and the second camera (42) are placed fairly distant from the active part of the tools to give good visibility within the action field of the tools.

The pot tending module is provided with tools other than the anode grabs:
a) a chipping hammer (13);
b) a bucket wheel (12);
c) a hopper (14) associated with a retractable duct (15).

The second camera (42) can easily display all the tending module tools. In the particular geometric configuration of the tending module in this example, this is achieved by having the elevation movement angle of said second camera (42) between −60° and +30° (anti-clockwise direction) with respect to the vertical plane P2. Similarly, the movement angle of the second camera (42) in azimuth is between 0 and −80° from the horizontal plane, so that the tool can be monitored as it moves downwards towards the working area or as it moves upwards from it. The magnification factor of the second camera (42) in zoom is between 1 and 25.

The first camera (41) is placed on the PTM in the vertical plane (P1) at an elevation substantially equal to the safety level, typically equal to 3 meters, and located outside the most peripheral of the anode grabs (11), typically at a horizontal distance (D1) from it equal to approximately 1 meter.

The second camera (42) is placed on the PTM in the vertical plane (P2) at an elevation substantially equal to the safety level, typically equal to 3 meters, and in a position opposite the position of the face (F) of the grabs that, when the PTM is in position to work on two given anodes, corresponds to the face of the anode stems that will come into contact with the anode beam, at a horizontal distance (d2) from the centre of gravity (110) of the grabs equal to substantially 3 meters.

The images perceived by the digital cameras (41) and (42) are transmitted to an image central processing device connected to said cameras by shielded cables, and this device processes the received images such that it can associate them by grouping them in the form of a single digital image. A number identifying the pot tending module with which the image central processing device is associated is inset into at least one peripheral area of the image thus formed. This digital image is then compressed in the JPEG2000 format. The module is associated with a COFDM type transmission system.

The pot tending module (7) comprises a chassis (8) and a turret (9) mounted on the chassis so that during use it can be pivoted about a vertical axis (A) and provided with two cameras (41) and (42), in a fixed position with respect to the tools. It also includes a third camera (43) placed not far from the second camera (42) and that will continuously display an overview of the tools in the module and the working area. A fourth camera (44) is located close to the base of the actuator (111) of one of the anode grabs (11). It aims at a zone (23) that encompasses the low positions of the anode grabs (11) and (11').

The pot tending module (7) is associated with a system for assistance with controlling handling and work operations on an electrolytic cell, designed for replacement of the anodes. Said system comprises the tending unit described above, a control module provided with at least one monitor reproducing the image of the working area filmed by at least one camera and a control module transmitting orders to actuators of the tending unit.

The instrumentation module comprises a 21" monitor that simultaneously displays images of the two first cameras (41 and 42) on a 15" diagonal. Each image is provided on a format of 1024*768 pixels.

The instrumentation module is also provided with a 17" screen providing a simultaneous continuous view of fields filmed by the third and the fourth cameras.

The control module is in the form of an easily portable remote control box provided with buttons. It controls movement of the travelling crane, the trolley, the turret(s) of the tending module, the cameras and the tools, preferably mounted on telescopic arms. Controls are transmitted to the different tending unit elements actuators using a conventional matched radio controls system.

The potroom is provided with a plurality of instrumentation modules located in fixed cabs, each cab being associated with a group of 4 cells. The control module is carried by the operator who moves to the cab associated with the cell affected by the anode change. The operator installs said control module in the cab, connecting it such that the control assistance system is completed in said cab and can thus function.

What is claimed is:

1. Pot tending module for a series of electrolytic cells intended for aluminum production by igneous electrolysis comprising a chassis to be fixed onto a mobile assembly and provided with a set of tools including in particular at least one anode handling device, the pot tending module being also provided with at least two display means capable of taking views and transmitting the views in the form of electromagnetic signals, a first display means being located to aim at a working area of an electrolytic cell along a first viewing direction (D1) of a straight line contained in a vertical plane (V1) and a second display means being located to aim at said working area along a second viewing direction (D2) of a straight line contained in a vertical plane (V2) not parallel to (V1), said planes (V1) and (V2) intersecting in a vertical straight line passing through said working area, said vertical planes (V1) and (V2) forming an angle greater than 45°.

2. Pot tending module according to claim 1, wherein the at least one anode handling device is a grab provided with two gripping devices that pivot about a direction (P) and one of the two said viewing directions D1 or D2 is substantially parallel to said direction (P).

3. Pot tending module according to claim 1, wherein said first and second viewing directions (D1) and (D2) substantially correspond to directions X and Y of large and small sides of the electrolytic cell once the pot tending module is positioned to work on a given anode.

4. Pot tending module according to claim 1, wherein said at least one anode handling device is designed to grip an anode stem with a rectangular section, and said first and second viewing directions (D1) and (D2) of the two display means substantially correspond to directions (L) and (l) of sides of a rectangular section of the anode stem when said pot tending module is positioned to work on a given anode.

5. Pot tending module according to claim 1, provided with several aligned anode handling devices, the first display means being located in a first vertical plane (P1) that contains an alignment direction of the handling devices, the second display means being located in a second vertical plane (P2) substantially perpendicular to the previous plane and passing through the centre of gravity of said handling devices.

6. Pot tending module according to claim 1, wherein said display means are located on or slightly above a safety level (S) that defines the elevation above which any lower end of the tool must be when said pot tending module has to move above the electrolytic cells.

7. Pot tending module according to claim 1, wherein the second display means is motor driven in elevation, in azimuth and in zoom.

8. Pot tending module according to claim 1, further comprising at least one of the tools:
   a) a chipping hammer;
   b) a bucket wheel;
   c) a hopper associated with a retractable duct; and
   d) a heavy lifting tool.

9. Pot tending module according to claim 1, wherein said first display means is located outside a most peripheral of the handling devices.

10. Pot tending module according to claim 5, wherein said second display means is located on the second plane P2 in a position that is on the opposite side of the position of the centre of gravity of said handling devices from a face (F) of the corresponding grab from that, when the pot tending module is in position to work on a given anode, corresponds to the face of an anode stem that will come into contact with an anode beam.

11. Pot tending module according to claim 1, comprising a chassis that can be fixed to a trolley and a turret mounted on the chassis so as to be able to rotate about a vertical axis (A) when in use, said turret being provided with a specific set of tools and with said two display means.

12. Pot tending module according to claim 1, comprising a chassis, that can be fixed to a trolley, a first turret mounted on the chassis so as to be able to rotate about a vertical axis when in use, said first turret being provided with a specific set of tools, and a second turret that surrounds said first turret and that can rotate about the same vertical axis, and on which said two display means are fixed.

13. Pot tending module according to claim 1, comprising a third display means, located not far from the second display means, said third display means being intended for displaying an overview of the tools of said pot tending module and the working areas for these tools.

14. Pot tending module according to claim 1, comprising a further display means located close to an actuator of one of said at least one anode handling device, and aimed at a zone that includes a low position of said at least one anode handling devices.

15. Pot tending module according to claim 1, wherein images perceived at least by the first and second display means are transmitted to a transmission system, to result in the creation of images displayed on screens placed outside said pot tending module.

16. Pot tending module according to claim 15, provided with a central image processing device connected to the display means and that processes perceived images to associate the images by grouping in the form of a single digital video image, and provided with a transmitter that transmits signals associated with the single digital video image in the form of electromagnetic waves to at least one receiver located outside said pot tending module.

17. Pot tending module according to claim 16, wherein said central image processing device processes images perceived at least by the first and second display means such that a number identifying the pot tending module with which the central image processing device is associated is inset into at least one peripheral area of the single digital video image thus transmitted and/or wherein said transmitter transmits in a specific frequency or a plurality of frequencies identifying said pot tending module.

18. Pot tending machine comprising a mobile element and a pot tending module according to claim 1.

19. Pot tending unit comprising a travelling crane that can be translated above the electrolytic cells and at least one pot tending machine comprising a trolley that can move along said travelling crane, and a pot tending module according to claim 1.

20. Method for performing work on electrolytic cells constructed and arranged for the production of aluminum by igneous electrolysis, utilizing a pot tending module according to claim 19.

21. Method according to claim 20, wherein at least one specific anode is replaced by a new anode.

* * * * *